United States Patent [19]

Kaplan et al.

[11] Patent Number: 4,910,301

[45] Date of Patent: * Mar. 20, 1990

[54] CEFEPIME CEPHALOSPORIN SALTS

[75] Inventors: Murray A. Kaplan, Syracuse, N.Y.; Thomas W. Hudyma, Durham, Conn.; Robert A. Lipper, Manlius, N.Y.; Kun M. Shih, East Syracuse, N.Y.; Susan D. Boettger, Syracuse, N.Y.

[73] Assignee: Bristol-Myers Company, New York, N.Y.

[ * ] Notice: The portion of the term of this patent subsequent to Sep. 27, 2000 has been disclaimed.

[21] Appl. No.: 144,899

[22] Filed: Jan. 19, 1988

Related U.S. Application Data

[63] Continuation-in-part of Ser. No. 901,088, Aug. 27, 1986, abandoned, which is a continuation-in-part of Ser. No. 762,235, Aug. 5, 1985, abandoned.

[51] Int. Cl.$^4$ .............................................. C07D 501/46
[52] U.S. Cl. ................................................... 540/222
[58] Field of Search ........................ 514/202; 540/222

[56] References Cited

U.S. PATENT DOCUMENTS

| | | | |
|---|---|---|---|
| 4,104,391 | 8/1978 | Cise | 540/227 |
| 4,316,018 | 2/1982 | Yoshimura | 540/227 |
| 4,329,453 | 5/1982 | Brodie | 540/225 |
| 4,406,899 | 9/1983 | Aburaki | 514/202 |
| 4,749,694 | 6/1988 | Fix | 514/202 |
| 4,751,295 | 6/1988 | Oka | 540/222 |
| 4,791,196 | 12/1988 | Ide | 540/222 |
| 4,808,617 | 12/1989 | Kaplan | 540/222 |

*Primary Examiner*—Donald G. Daus
*Attorney, Agent, or Firm*—Robert E. Carnahan

[57] ABSTRACT

Crystalline sulfuric, di-nitric, mono-hydrochloric, di-hydrochloric, and di- and sesqui-orthophosphoric acid addition salts of 7-[α-(2-aminothiazol-4-yl)-α-(Z)-methoxyiminoacetamido]-3-[(1-methyl-1-pyrrolidinio)-methyl]-3-cephem-4-carboxylate are stable even at elevated temperatures. The crystalline sulfuric acid addition salt is made by forming an admixture of (a) at least one molar equivalent of sulfuric acid with (b) zwitterion in an amount so as to be present in the admixture at a concentration of greater than 25 milligrams/ml, causing crystallization, separating the crystals, washing and drying. The crystalline monohydrochloride, dihydrochloride, and orthophosphate salts are prepared by dissolving the zwitterion in the appropriate amount of acid, causing crystallization by adding acetone and isolating the crystals. Physical admixtures of the salts with certain bases in proportions to give a pH ranging from about 3.5 to about 7 on dilution with water provide injectable compositions on dilution.

10 Claims, 4 Drawing Sheets

CEFEPIME CEPHALOSPORIN SALTS

TECHNICAL FIELD

This invention is directed to temperature stable semisynthetic cephalosporin salts whose preparation has not been described in the literature, to the preparation of such salts, and to admixtures containing these salts.

BACKGROUND OF THE INVENTION

Aburaki et al. U.S. Pat. No. 4,406,899 discloses 7-[α-(2-aminothiazol-4-yl)-α-(Z)-methoximinoacetamido]-3-[(1-methyl-1-pyrrolidinio)methyl]-3-cephem-4-carboxylate in the zwitterion form and mentions corresponding acid addition salts (which are present in the zwitterion form in injectable compositions) and shows that the zwitterion form has broader spectrum activity than ceftazidime and cefotaxime.

However, the aforementioned Aburaki et al. cephalosporins are stable only for a few hours as injectable compositions and the zwitterion form even as a dry powder is unstable at room temperature and loses 30% or more of its activity on storage at elevated temperatures (e.g. 45 deg. C. and above) for even one week and therefore requires special insulated packaging and/or refrigeration and is at a packaging and storage disadvantage compared to ceftazidime and cefotaxime.

While Aburaki et al. mentions acid addition salts, the patent does not state how to make these or state which if any of these salts have good stability in dry powder form. Kessler et al., "Comparison of a New Cephalosporin, BMY 28142, with Other Broad-Spectrum β-Lactam Antibiotics", *Antimicrobial Agents and Chemotherapy*, Vol. 27, No. 2, pp. 207–216, Feb. 1985 mentions the sulfate salt, but does not disclose how to prepare such or that this salt has room temperature stability and good elevated temperature stability in dry powder form.

SUMMARY OF THE INVENTION

It has been discovered herein that certain crystalline acid addition salts of 7-[α-(2-aminothiazol-4-yl)-α-(Z)-methoxyiminoacetamido]-3-[(1-methyl-1-pyrrolidinio)-methyl]-3-cephem-4-carboxylate in dry powder form have excellent room temperature stability and have superior elevated temperature stability compared to the zwitterion form. The term "dry powder form" as used herein means a moisture content of less than 5% by weight when measured by loss in weight on drying at atmospheric pressure and a temperature of less than 70° C.

These acid addition salts are the crystalline salts of 7-[α-(2-aminothiazol-4-yl)-α-(Z)-methoxyiminoacetamido]-3-[(1-methyl-1-pyrrolidinio)methyl]-3-cephem-4-carboxylate selected from the group consisting of the sulfuric, di-nitric, mono-hydrochloric, and di-hydrochloric acid addition salts and orthophosphoric acid addition salts (1.5–2 moles of orthophosphoric acid per mole of salt, e.g. a range of from the sesqui- to the di-orthophosphoric acid salts), or solvates thereof.

The acid addition salts herein when formed into aqueous injectable compositions and adjusted to pH 6.0 provide the zwitterion in solution. The zwitterion has the structure

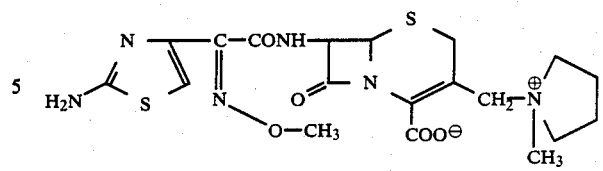

The broad spectrum utility against various organisms of the zwitterion form, and thus of aqueous compositions made up from the salts herein, is shown by the data in Aburaki et al. U.S. Pat. No. 4,406,899.

Aqueous compositions made up from the acid addition salts herein simply by the addition of sterile water provide acidic solutions which provoke unacceptable irritation on intravenous administration to rabbits and unacceptably painful sensation on intramuscular administration to rabbits. The sulfuric acid and di-nitric acid addition salts have reduced solubilities which are insufficient for typical injectable compositions. It has been found herein that these objectionable characteristics are overcome by utilizing the salts herein in physical admixture (that is as an admixture of solids) with a pharmaceutically acceptable non-toxic organic or inorganic base in proportions to provide a pH of about 3.5 to about 7 on dilution with water to a zwitterion activity of from 1 mg/ml to 400 mg/ml, normally 250 mg/ml (as determined by high performance liquid chromatography, hereinafter HPLC).

The preferred salt for use as a manufacturing intermediate is the crystalline sulfuric acid addition salt. It is preferred because its low solubility in water (25 mg/ml) allows high recovery from aqueous medium on crystallization, and good purity.

The crystalline sulfuric acid addition salt is readily prepared by a process comprising the steps of (a) forming an admixture of (i) at least 1 molar equivalent of sulfuric acid and (ii) zwitterion in an amount so as to be present in the admixture at a concentration greater than 25 mg/ml, (b) causing crystallization of the sulfuric acid addition salt to occur, and (c) isolating crystalline sulfuric acid addition salt.

DETAILED DESCRIPTION

Figure 1:
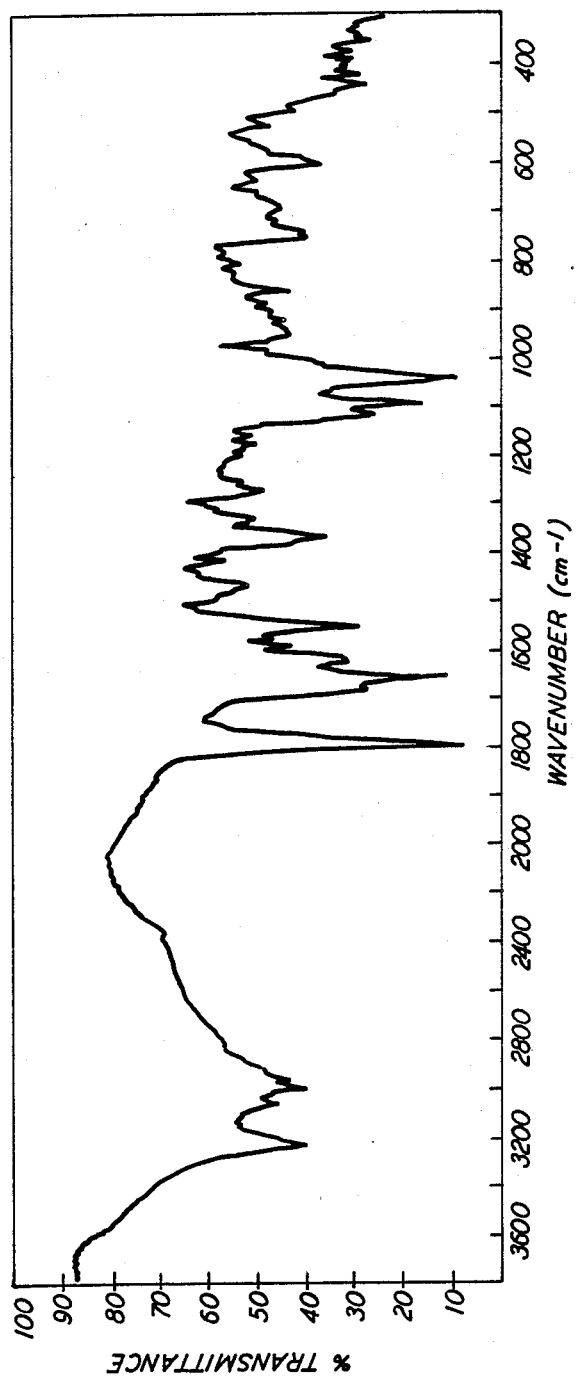
FIG. 1 is a graphical representation of the infra red absorption spectrum of crystalline 7-[α-(2-aminothiazol-4-yl)-α-(Z)-methoxyiminoacetamido]-3-[(1-methyl-1-pyrrolidinio)methyl]-3-cephem-4-carboxylate sulfate salt measured on a KBr dilution thereof.

The crystalline salts herein (hereinafter referred to simply as the salts herein) have excellent stability at room temperature and have a potency loss (as determined by HPLC), of less than 1% on storage for a month at room temperature. These salts also have excellent stability at elevated temperatures and have a potency loss (as determined by HPLC) of less than 15% on storage for a month at 45–56 deg. C.

The sulfuric acid addition salt is a preferred salt herein. It has a potency loss of less than 10% on storage for a month a 45–56 deg. C. Very importantly, it has a low solubility in water, i.e. about 25 mg/ml, and therefore is crystallized from water with minimized residual loss.

The di-nitric acid addition salt herein also has a low solubility in water, i.e. about 60 mg/ml, and therefore also provides low residual loss on crystallization from water.

The mono-hydrochloric, di-hydrochloric and sesqui- or di-orthophosphoric acid addition salts have water solubilities greater than 200 mg/ml., and therefore are preferably crystallized from organic solvents, rather than from water, in order to obtain good yields.

We turn now to the preparation of the salts herein.

As previously indicated the sulfuric acid addition salt herein is prepared by a process comprising the steps of (a) forming an admixture of (i) at least one molar equivalent of sulfuric acid and (ii) zwitterion corresponding to said salt in an amount so as to be present in the admixture at a concentration of greater than 25 mg/ml, (b) causing crystallization to occur, and (c) isolating crystalline sulfuric acid addition salt. Preferably the zwitterion is used in step (a) in an amount so as to be present in the admixture at a concentration ranging from about 100 mg/ml to about 200 mg/ml, and step (b) is carried out in an aqueous medium free of organic solvent. Normally no more than 2 molar equivalents of sulfuric acid are utilized in step (a). Normally zwitterion is used in step (a) in an amount so as to be present in the admixture at a concentration less than 500 mg/ml.

Step (a) is readily carried out either by adding solid zwitterion to sulfuric acid solution (e.g. 1N $H_2SO_4$) with rapid stirring to form a solution. Alternatively step (a) can be carried by dissolving solid zwitterion in water and slowly adding sulfuric acid with stirring to form a solution.

Step (b) is carried out by inducing crystallization, preferably by seeding, and then slurrying, preferably for 15 minutes to 2 hours. It is preferred that this crystallization step be carried out in aqueous medium, free of organic solvent, and in such case purities greater than 98% are normally obtained. While the presence of organic solvent, such as acetone, fosters crystallization and increases yield by lowering the solubility of the formed sulfuric acid addition salt in the crystallization medium, it also can foster precipitation of impurities resulting in decreased purity. When the zwitterion is used in step (a) in an amount so as to be present in the admixture in an amount less than 25 mg/ml, organic solvent, preferably acetone, must be included in the crystallization medium to provide reasonable recovery. When acetone is used, it is appropriately used in amounts of 0.5 to 10 volumes per volume of aqueous crystallization medium.

Step (c) is carried out by separating the crystals from the crystallization medium, preferably by vacuum filtration, then washing e.g. with acetone/water followed by acetone alone or 0.1N sulfuric acid (e.g. 1/10 volume) followed by acetone (e.g. ¼ volume), and then drying, e.g. by vacuum drying at 30–50 deg. C. for 4–20 hours.

The method herein for forming the sulfuric acid addition salt results in the purification of the zwitterion form because of the limited solubility of the sulfuric acid addition salt compared to the zwitterion form and can be used to purify zwitterion without isolating it as a solid. If it is desired to obtain substantially pure zwitterion (free-base) from the formed sulfuric acid addition salt, this can be carried out by dissolving the salt in water, adding $Ba(OH)_2 \cdot 8H_2O$ in an amount of 90–100% of theory at a pH of less than 6.5 to precipitate $BaSO_4$, filtering to remove the $BaSO_4$ and recovering the filtrate containing the zwitterion dissolved therein and utilizing it as a solution or isolating solid zwitterion (free-base) by lyophilizing it or by adding acetone to precipitate amorphous zwitterion followed by isolating solid zwitterion by vacuum filtration, washing e.g. with acetone, and vacuum drying. Alternatively, the sulfuric acid addition salt is converted to the free-base utilizing ion exchange resins, e.g. Dowex WGR (a weak base anion exchange resin) and Dowex XU-40090.01 (a strong acid cation exchange resin) with subsequent lyophilization.

Turning now to the preparation of the crystalline di-nitric acid addition salt herein, this is obtained by admixing (i) at least two molar equivalents of nitric acid and (ii) zwitterion corresponding to said salt so to be present in the admixture at a concentration greater than 100 mg/ml, and then inducing crystallization by seeding or rubbing with a glass rod, diluting with 2-propanol and cooling. The crystalline di-nitric acid addition salt is recovered e.g. by filtering, washing sequentially, e.g. with 2-propanol-$H_2O$ (50% v/v), 2-propanol, and ether, and then vacuum drying at 50 deg. C. for 2 hours.

The mono-hydrochloric acid addition salt herein is prepared by dissolving zwitterion in approximately one molar equivalent of hydrochloric acid and causing crystallization by adding acetone with stirring and continuing to stir, followed by isolating crystals, e.g. by vacuum filtration followed by washing with acetone and vacuum drying. Alternatively the mono-hydrochloric acid addition salt is formed from the di-hydrochloric acid addition salt by slurrying the di-hydrochloric acid addition salt in methylene chloride and adding 1 mole equivalent of triethylamine followed by slurrying to form the mono-hydrochloric acid addition salt which is isolated, e.g. by vacuum filtration, followed by washing with methylene chloride and vacuum drying.

The crystalline di-hydrochloric acid addition salt herein is prepared by dissolving zwitterion in at least two molar equivalents of hydrochloric acid, then causing crystallization by adding acetone, then isolating crystals e.g. by vacuum filtration, washing with acetone and vacuum drying.

The crystalline di-orthophosphoric acid addition salt herein is prepared by dissolving the zwitterion in at least 2 molar equivalents of phosphoric acid, causing crystallization by adding acetone, and isolating crystals by e.g. by vacuum filtration followed by washing first with acetone and then with ether and then vacuum drying. The crystalline sesqui-orthophosphoric acid addition salt is formed by this same procedure except that about 1.5 molar equivalents of phosphoric acid is used, and methanol is preferably used to foster crystallization.

The salts herein are formed into injectable compositions by diluting with sterile water and buffering to a pH of 3.5–7 to form an injectable concentration of 1 mg/ml up to 400 mg/ml of zwitterion. Suitable buffering agents include, for example, trisodium orthophosphate, sodium bicarbonate, sodium citrate, N-methylglucamine, L(+) lysine and L(+) arginine. For intramuscular or intravenous administration to an adult human, a total dosage of from about 750 to about 3000 mg per day in divided doses is normally sufficent.

The salts herein are not desirably formed into injectable compositions simply by the addition of sterile water because the sulfuric and di-nitric acid addition salts are not sufficiently soluble to form compositions of normal concentration for administration and because the salts herein when dissolved provide very low pH compositions (1.8–2.5) which provide painful sensation on injection. As indicated above, it has been found herein that these shortcomings are overcome by forming the salts herein into a physical, i.e. solid, admixture with pharmaceutically acceptable, normally solid non-toxic organic or inorganic bases in proportions to provide a pH ranging from about 3.5 to about 7, preferably from about 4 to about 6, on dilution of the admixture with water to injectable concentration of 1 mg/ml up to 400 mg/ml of zwitterion, e.g. zwitterion activity of 250 mg/ml as determined by HPLC assay.

The exact proportions of ingredients in the physical admixture vary from lot to lot of the salt since the purity of the salt varies from lot to lot. The proportions of ingredients are established for a particular lot by pretitrating in respect to a sample to obtain a selected pH within the aforementioned range.

The physical admixture is readily stored and shipped in solid form thereby taking advantage of the stability of the salts herein and is readily converted into an injectable composition simply by addition of water, e.g. by a nurse or doctor just prior to use.

The physical admixture is prepared by blending the salt and the base into a uniform blend, e.g. utilizing a standard blender in a dry atmosphere, and is then preferably filled into a vial or other container, all under aseptic conditions.

The bases for use in the admixture include, for example, trisodium orthophosphate, sodium bicarbonate, sodium citrate, N-methylglucamine, L(+) lysine and L(+) arginine. L(+) lysine and L(+) arginine are preferred since admixtures containing these are reconstituted to provide injectable compositions which on injection provide less pain in animals than compositions derived from admixtures containing other bases. The L(+) arginine is very preferably utilized in a proportion to provide a pH of 3.5–6 on dilution of the admixture with water to provide a composition with a zwitterion activity of 250 mg/ml (as determined by HPLC assay).

The salts herein and substantially dry physical admixtures containing them can be stored without refrigeration or insulated packaging and still retain high potency.

In several of the preparations herein the unstable zwitterion is used as the starting material. The preparation of this is described in Examples 1–3 of Aburaki et al. U.S. Pat. No. 4,406,899. The zwitterion is referred to in Aburaki et al. as 7-[(Z)-2-methoxyimino-2-(2-aminothiazol-4-yl)acetamido-3-[(1-methyl-1-pyrrolidinium)-methyl]-3-cephem-4-carboxylate.

The invention is illustrated in the following working examples.

EXAMPLE I

Preparation of the Sulfuric Acid Addition Salt 1.5 g of zwitterion are added slowly to 10 ml of rapidly stirred 1N $H_2SO_4$ (1.59 molar equivalents) at 20–26 deg. C. A solution is obtained. Crystallization is then induced by seeding with crystalline sulfuric acid addition salt and the crystalline mass is slurried for 0.5 hours. The crystals are then separated by vacuum filtration, washed with 3 ml of 50% acetone/water (V/V) and with two 5 ml portions of acetone, and vacuum dried at 40–50 deg. C. overnight.

A typical yield is 1.3 g of sulfuric acid addition salt. Analysis: Calculated for $C_{19}H_{24}N_6O_5S_2 \cdot H_2SO_4$: %C, 39.44; %H, 4.53; %N, 14.52; %S, 16.62; %$H_2O$, none. Found: %C, 38.91; %H, 4.57; %N, 14.64; %S, 16.71; %$H_2O$, 1.42.

EXAMPLE II

Preparation of the Sulfuric Acid Addition Salt 1.5 g of zwitterion are dissolved in 5 ml of water. 5 ml of 1M $H_2SO_4$ are slowly added to this solution with stirring. Crystallization is then induced by seeding with crystalline acid addition salt and the crystalline mass is slurried for 0.5 hours. The crystals are then separated by vacuum filtration, washed with 3 ml of 50% acetone/water (V/V) and with two 5 ml portions of acetone, and vacuum dried at 40–50 deg. C. overnight.

The typical yield is 1.3 g of sulfuric acid addition salt.

EXAMPLE III

Preparation of the $(HNO_3)_2$ Acid Addition Salt 300 mg of zwitterion are dissolved in 2N nitric acid (0.5 ml). The solution is rubbed with a glass rod, diluted with 2-propanol (0.4 ml) and cooled. The crystalline title compound is collected and is sequentially washed with 0.4 ml of 2-propanol $H_2O$ (1:1), 2-propanol and then ether to afford 127 mgs of the dinitrate salt.

Analysis: Calculated for $C_{19}H_{24}N_6O_5S_2 \cdot 2HNO_3$: %C, 37.62; %H, 4.32; %N, 18.47; %S, 10.57. Found: %C, 36.92; %H, 4.10; %N, 18.08; %S, 10.67; ($H_2O$ content 0.90%).

EXAMPLE IV

Preparation of the Monohydrochloride Acid Addition Salt 1 g of zwitterion is dissolved in 2.08 ml of 1N HCl (1 molar equivalent) at 20–25 deg. C. Thirty ml of acetone are added with rapid stirring over a 15 minute period whereby crystals form. Stirring is continued for 1 hour. The crystals are isolated by vacuum filtration, washed with 10 ml of acetone and vacuum dried at 50 deg. C. for 2 hours.

A typical yield is 0.9 g of crystalline monohydrochloride salt. Analysis: Calculated for $C_{19}H_{24}N_6O_5S_2 \cdot HCl$: %C, 41.37; %H, 4.75; %N, 15.2; %S, 11.63; %Cl, 12.86. Found: %C, 39.32; %H, 4.88; %N, 13.95; %S, 11.28; %Cl, 12.44; %$H_2O$, 4.5. (Corrected for $H_2O$: %C, 41.17; %N, 14.61; %S, 11.82; %Cl, 13.03).

EXAMPLE V

Preparation of the Dihydrochloride Acid Addition Salt and Preparation of the Monohydrochloride Acid Addition Salt From It 350 mg of zwitterion are dissolved in 2 ml of 1N-HCl. 10 ml of acetone are added to the resultant solution, with rapid stirring and over a 5 minute interval, whereby crystals form. Stirring is continued for 5 additional minutes. Then 10 additional ml of acetone are added and stirring is carried out for 0.5 hours. The crystals are removed by vacuum filtration, washed with two 5 ml portions of acetone and vacuum dried at 40–45 deg. C. for 24 hours.

A typical yield is 300 mg of crystalline dihydrochloride acid addition salt. Analysis Calculated for $C_{19}H_{24}N_6O_5S_2 \cdot 2HCl$: %C, 41.38; %H, 4.75; %N, 15.2; %S, 11.62; %Cl, 12.8. Found: %C, 40.78; %H, 4.98; %N, 14.7; %S, 11.25; %H$_2$O, 1.25. (Corrected for H$_2$O: %C, 41.1; %N, 14.88; %S, 11.39; %Cl, 11.94).

1 g of dihydrochloride salt prepared as above is slurried in 20 ml of methylene chloride at 20–25 deg. C. in a sealed flask and 0.28 ml of triethylamine is added over a 15 minute interval. The crystalline mass is then slurried for 5 hours. The resultant monohydrochloride crystals are then isolated by vacuum filtration, washed with two 5 ml portions of methylene chloride and vacuum dried at 50 deg. C. for 2 hours. A typical yield is 800 mg.

EXAMPLE VI

Preparation of the Di-orthophosphoric Acid Addition Salt 1 g of zwitterion is dissolved in 3.4 ml of 144 mg/ml H$_3$PO$_4$ (2.2 molar equivalents) at 15 deg. C. The resulting solution is suitably filtered to clarify it. 12 ml of acetone are added to the clarified solution, with rapid stirring and over a 10 minute period whereby crystals form. Stirring is continued for 10 minutes. Then 30 ml of acetone are added over a 10 minute period, and stirring is continued for an additional 15 minutes. The crystals are collected by vacuum filtration, washed with two 5 ml portions of acetone and two 5 ml portions of ether and dried under high vacuum for 16 hours.

A typical yield for this type of preparation was 1.1 g of crystalline di-orthophosphoric acid addition salt. Analysis: Calculated for $C_{19}H_{24}N_6O_5S_2 \cdot 2H_3PO_4$: %C, 33.72; %H, 4.47; %N, 12.42. Found: %C, 33.43; %H, 4.65; %N, 12.02; %H$_2$O, 1.82. (Corrected for H$_2$O: %C, 34.0; %N, 12.2).

The sesqui-orthophosphoric acid addition salt is formed as described above except that methanol is preferably used in place of all other solvents. This is a desirable salt for pharmaceutical dosage form use.

EXAMPLE VII

Stabilities at Elevated Temperatures

Elevated temperature stabilities were determined by storing the preparations in dry containers at temperatures and for time periods as denoted below and potency losses or gains were determined by HPLC. A % potency gain is indicated by a plus sign in front of a figure. A less than 10% potency loss over a 2 to 4 week period at 45–56 deg. C. is usually indicative of less than 10% potency loss over a 2–3 year period at room temperature.

| Form | 45 Deg. C. (Weeks) | | | 56 Deg. C. (Weeks) | | | 100 Deg. C. (Days) |
|---|---|---|---|---|---|---|---|
| | 1 | 2 | 4 | 6 | 1 | 2 | 4 | 1 |
| Zwitterion | 37 | 51 | 71 | — | 57 | — | — | 100 |
| H$_2$SO$_4$ Salt | 2.4 to +5 | 3 | +5 | 1.4 | 5 to +6 | +3 | 0 to +6 | 0–10 |
| (HNO$_3$)$_2$ Salt | 8.8 | | 3.4 | 0.68 | 10.3 | 3.7 | 2.4 | — | — |
| HCl Salt | 4.8 | | 2.3 | 6.0 | 6.4 | 6.4 | — | — | — |
| (HCl)$_2$ Salt | 0 | | — | 7.4 | — | 0 | — | 7.2 | 12.4 |
| (H$_3$PO$_4$)$_2$ Salt | 0 | | 3.0 | 1.0 | — | 2.7 | 5.0 | — | — |

EXAMPLE VIII

Testing of Physical Admixtures

Physical admixtures were made up of crystalline sulfuric acid salt with (a) trisodium orthophosphate, (b) sodium bicarbonate, (c) L(+) lysine, and (d) L(+) arginine. The bases were added in proportions to provide pH's on dilution of the admixture with water to a zwitterion activity of 250 mg/ml (as determined by HPLC assay) as follows: trisodium orthophosphate (to provide a pH of 6.0); sodium bicarbonate (to provide a pH of 6.0); L(+) lysine (to provide a pH of 6.0); L(+) arginine (to provide a pH of 6.0). Injectable compositions were made up by reconstituting with sterile water to a zwitterion activity of 250 mg/ml as determined by HPLC assay. There were no solubility problems. Injections (100 mg/kg) were carried out intramuscularly on rabbits with pain within acceptable thresholds. The least pain was with the arginine containing composition.

Similar results of good solubility and acceptable pain on intramuscular injection are obtained on use of the other salts herein in the physical admixtures with the above bases.

FIG. 1 is the infra red absorption spectrum of the crystalline sulfate salt prepared as described in Examples I or II pelletized in the crystalline form with potassium bromide.

The X-ray powder diffraction pattern of the crystalline sulfate salt of 7-[α-(2-aminothiazol-4-yl)-α-(Z)-methoxyiminoacetamido]-3-[(1-methyl-1-pyrrolidinio)-methyl]-3-cephem-4-carboxylate prepared as described in Example I or II was determined with a Rigaku Powder Diffractometer using a copper target X-ray tube, a nickel filter, and the sample contained in a glass dish. The scan rate was 2 deg./min. over the range from 5 deg. to 40 deg. and a chart was mechanically recorded to show the angles of maximum diffraction. From this the (d) spacings and relative intensities (I/I$_o$) were calculated. They are listed below.

| d spacing (A) | I/I$_o$ (%) |
|---|---|
| 9.20 | 100 |
| 6.80 | 50 |
| 5.50 | 28 |
| 5.09 | 22 |
| 4.50 | 38 |
| 4.41 | 44 |
| 4.19 | 63 |
| 3.78 | 38 |
| 3.64 | 44 |
| 3.39 | 25 |
| 3.31 | 31 |

| d spacing (A) | I/I_o (%) |
|---|---|
| 3.15 | 47 |

EXAMPLE IX

Preparation of the Sesquiphosphate Salt

The zwitterion, 0.70 g., is dissolved with rapid stirring in from 2.2 to 2.4 ml. of 85% phosphoric acid (2.1 to 2.2 molar equivalents) which has been diluted 1:10 (v/v) with water. The solution is clarified by filtration through a 0.22-0.45 micron pore-size membrane filter. From 5 to 7 parts by volume (15-20 ml) of methanol is added to the filtrate with rapid stirring during a 30 to 60 min. period. Crystals form during this operation, and rapid stirring is continued for 1.5 to 2 hours. The crystalline product is recovered by vacuum filtration. The product is washed on the filter first with 6 to 8 ml of 1:1 (v/v) methanol: acetone taking care to maintain a tightly packed filter cake, and then with acetone. The product is dried in vacuo at 50° C. for 2 hours; typical yield 0.7 to 0.75 g.

Figure 2:
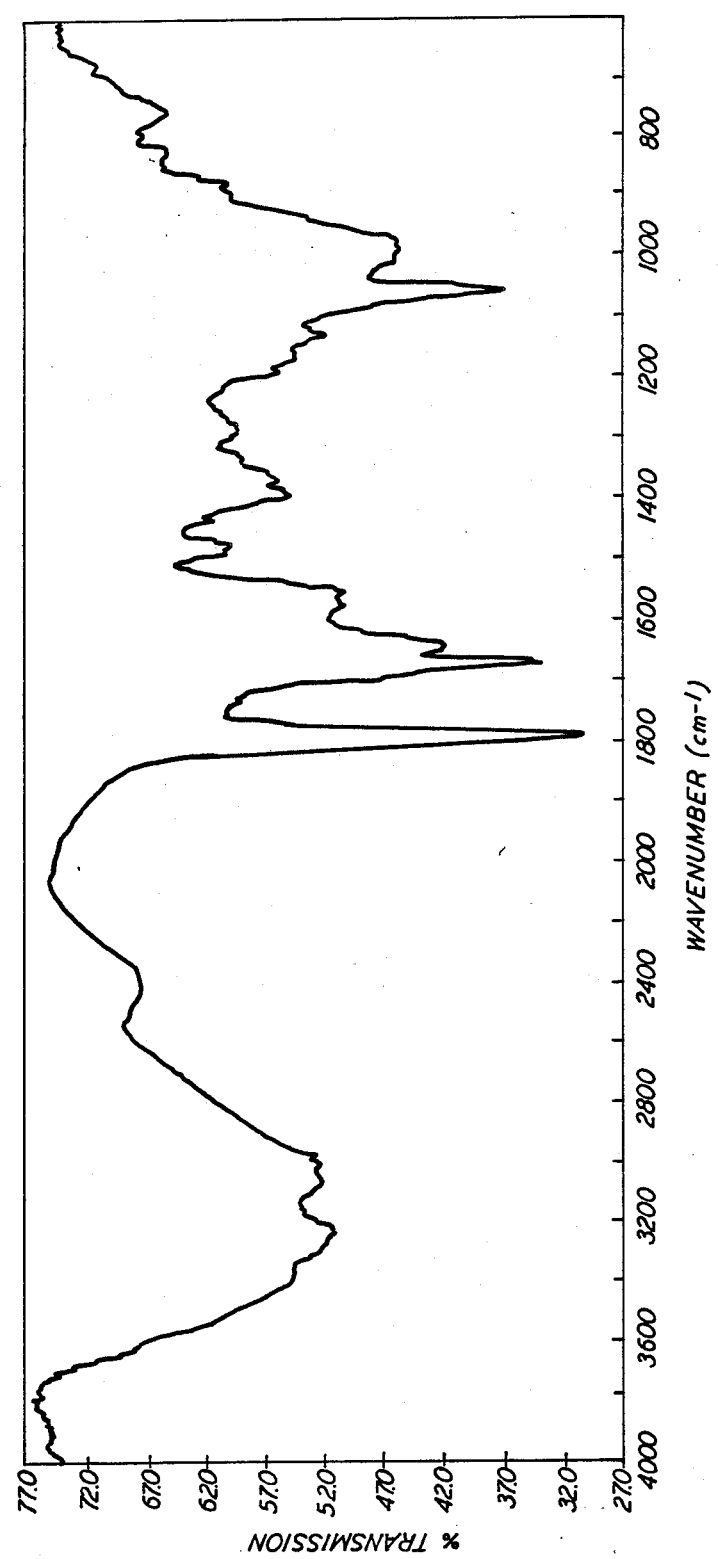
FIG. 2 is a graphical representation of the infra red absorption spectrum of the crystalline sesquiphosphate salt of 7-[α-(2-aminothiazol-4-yl)-α-(Z)-methoxyiminoacetamido]-3-[(1-methyl-1-pyrrolidinio)methyl]3-cephem-4-carboxylate measured on a KBr dilution thereof.
Figure 3:
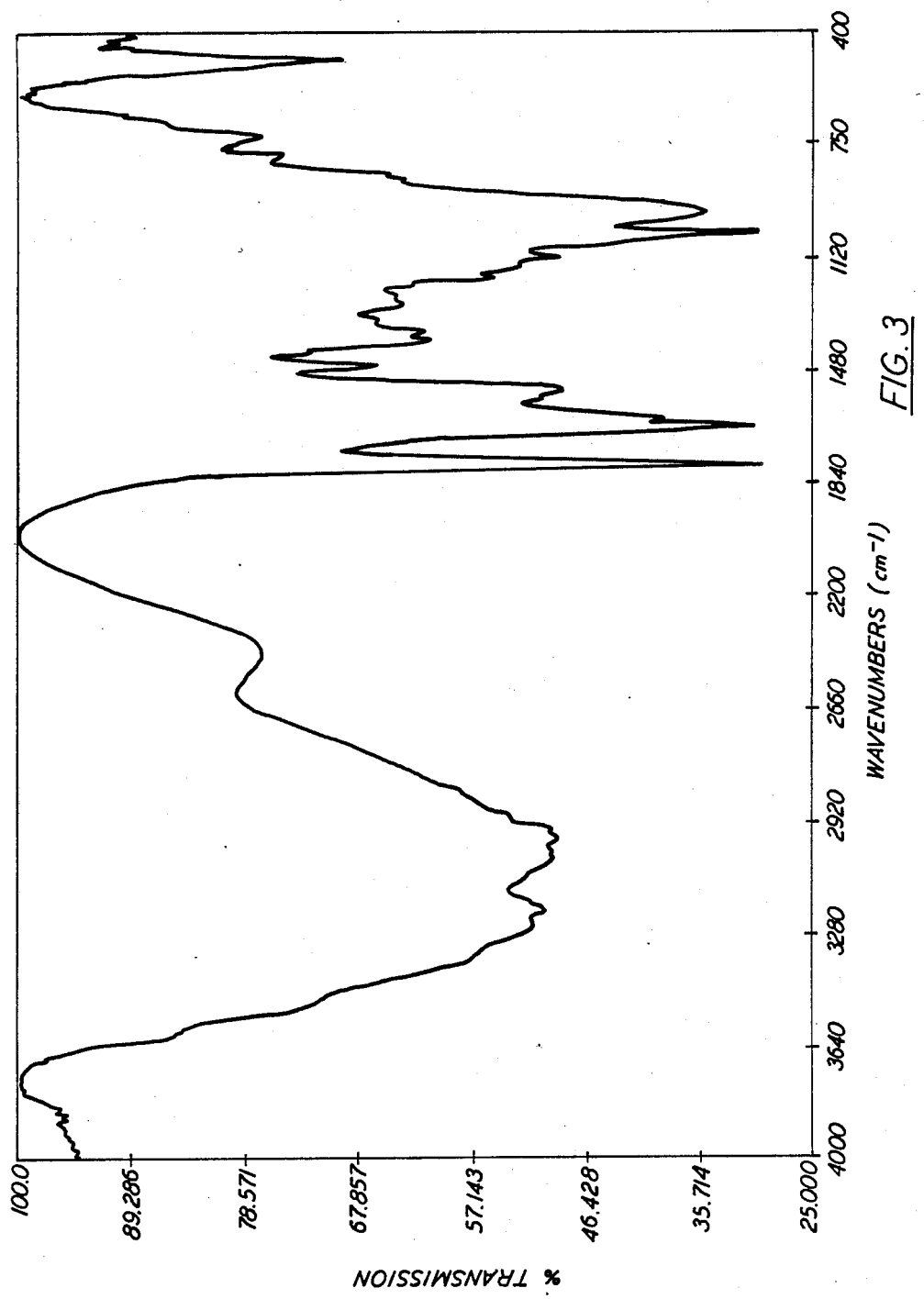
FIG. 3 is a graphical representation of the infra red absorption spectrum of the crystalline diphosphate salt of 7-[α-(2-aminothiazol-4-yl)-α-(Z)-methoxyiminoacetamido]-3-[(1-methyl-1-pyrrolidinio)methyl]-3-cephem-4-carboxylate measured on a KBr dilution thereof.
Figure 4:
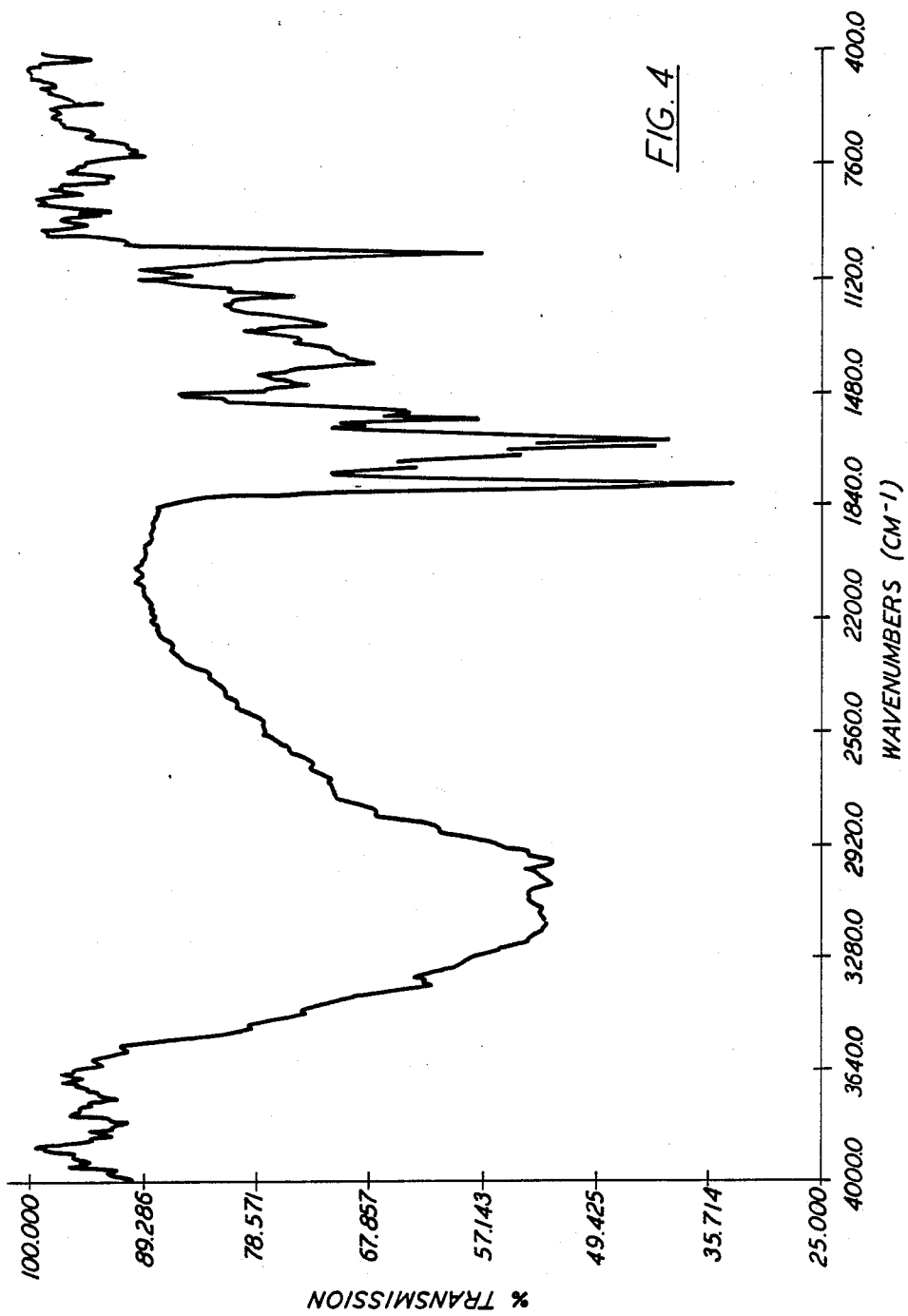
FIG. 4 is a graphical representation of the infra-red absorption spectrum of the crystalline dihydrochloride mono-hydrate of 7-[α-(2-aminothiazol-4-yl)-α-(Z)-methoxyiminoacetamido]-3-[(1-methyl-1-pyrrolidinio)-methyl]-3-cephem-4-carboxylate.

Infrared Interpretation (See FIG. 2) (IR, KBr pellet)

| Infrared Interpretation (See FIG. 2) (IR, KBr pellet) | |
|---|---|
| Peak Position (cm$^{-1}$) | Functional Group |
| 2800-3400 | NH,NH$_3^+$, carboxyl OH |
| 1780 | β-lactam C=O |
| 1680 | Carboxyl C=O |
| 1660 | Amide C=O |
| 1630 | C=N, C=C |
| 1550 | Amide OH |
| 980, 1040 | PO$_4^=$ |

Behavior on Heating

An exotherm is shown at 171.8° C. in the differential scanning calorimeter tracing.

X-Ray Diffraction Pattern

The X-ray powder diffraction pattern of the foregoing sesquiphosphate salt was measured with a Rigaku Powder Diffractometer in the same fashion as described above with respect to sulfate salt with the following results.

Sesquiphosphate Diffraction Pattern

| d | I/I_o (%) |
|---|---|
| 11.04 | 32 |
| 9.2 | 16 |
| 7.89 | 24 |
| 7.02 | 42 |
| 6.7 | 32 |
| 5.5 | 26 |
| 4.64 | 100 |
| 4.456 | 53 |
| 4.3 | 58 |
| 3.88 | 26 |
| 3.75 | 89 |
| 3.56 | 21 |
| 3.31 | 26 |
| 3.05 | 16 |

NMR Interpretation ($^1$H 90 MHz NMR, D$_2$O solution)

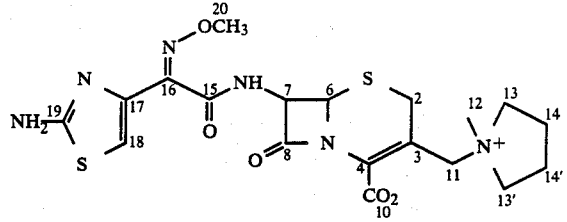

| Chemical Shift (ppm δ vs. TSP) | Description | Integral | Assignment |
|---|---|---|---|
| 2.0-2.4 | Multiplet | 4 | 14CH$_2$, 14'CH$_2$ |
| 3.04 | Singlet | 3 | 12CH$_3$ |
| 3.3-3.6 | Multiplet | 5 | 2CH, 13CH$_2$, 13'CH$_2$ |
| 3.94 | Doublet | 1 | 2CH |
| 4.12 | Singlet | 3 | 20CH$_3$ |
| 4.12 | Doublet | 1 | 11CH |
| 4.8 | Doublet | 1 | 11CH |
| 5.42 | Doublet | 1 | 6CH |
| 5.88 | Doublet | 1 | 7CH |
| 7.21 | Singlet | 1 | 18CH |

Stability

| Time-Temperature | % Loss |
|---|---|
| 1 day; 100° C. | 10.9 |
| 3 days; 70° C. | 0 |
| 7 days; 70° C. | 1.9 |
| 1 week; 56° C. | 1.0 |
| 2 weeks; 56° C. | 1.4 |
| 4 weeks; 56° C. | 0 |
| 1 week; 45° C. | 0 |
| 2 weeks; 45° C. | 1.4 |
| 4 weeks; 45° C. | 0.7 |
| 8 weeks; 45° C. | 1.6 |
| 1 month; 37° C. | 2.5 |

Elemental Analysis (Percent by Weight)

| | Found | Dry Basis | Theory (Sesquiphosphate) |
|---|---|---|---|
| C | 35.44 | 36.3 | 36.4 |
| H | 4.66 | 4.41 | 4.7 |
| N | 12.88 | 13.2 | 13.4 |
| H$_2$O | 2.29* | — | monohydrate = 2.8% H$_2$O |
| H$_3$PO$_4$ | 23.06 | 23.6 | 23.6 |

*Karl Fischer Method

EXAMPLE X

Methanol Crystallization of Phosphate Salt

Recrystallized sulfate salt, prepared as described in Example I or II hereof, 25 g., is dissolved in 400 ml of 1,1,2-trichloro-2,2,1-trifluoroethane (Freon TF) and the solution is treated with 50 ml of Amberlite LA-2 (Amberlite LA-2 is a water-insoluble, organic solvent soluble, aliphatic secondary amine whose mineral acid salts are also organic solvent soluble) and 50 ml of water. After vigorous stirring of the mixture for 70 min., the phases are separated and the aqueous phase containing the zwitterion is recovered following treatment thereof with a further 40 ml of Amberlite LA-2, extraction with an additional 310 ml of freon TF, treatment with decolorizing carbon, and filtration.

One-half of the foregoing aqueous solution of the zwitterion, volume 33.5 ml, is arranged in a stirred vessel and treated with 1.65 ml of 85% phosphoric acid. A further quantity of 1.65 ml of 85% $H_3PO_4$ is mixed with 90 ml of methanol and slowly added to the aqueous zwitterion solution during 30 min. at 25° C. A slurry of the desired sesquiphosphate salt forms, and stirring is continued at 25° C. for one hour. The product is then collected by suction filtration, washed with 30 ml of absolute ethanol, and then with 15 ml of methylene chloride, and dried in vacuo at 45° for 15 hours, yield 9.80 g. (72% on a bioassay basis of 7-[α-(2-aminothiazol-4-yl)-α-(Z)-methoxyiminoacetamido]-3-[(1-methyl-1-pyrrolidinio)methyl-3-cephem-4-carboxylate phosphate salt containing 1.5 molecular equivalents or $H_3PO_4$ and characterized by the differential scanning colorimeter tracing, infra red absorption spectrum, and X-ray diffraction pattern given herein.

EXAMPLE XI

Preparation of Dihydrochloride Monohydrate from Sulfate - Amine Process

(a) Conversion of Sulfate to Zwitterion

The sulfate salt prepared as described in Example 1, 300 g (0.581 mole), is added to an agitated mixture of Amberlite LA-2 (600.5 mL, 1.332 mole), Freon TF (4.5 L) and Water for Injection, USP (900 mL) and the mixture is stirred 1 h at 23° C. After phase separation, the organic layer is washed with water (225 mL) and the combined aqueous phases are stirred with a solution of Amberlite LA-2 (421 mL, 0.933 mole) in Freon TF (3.6 L) for 1 h at 23° C. The aqueous phase is extracted with Freon TF (2×375 mL) and the residual solvent removed by vacuum. The solution is treated with decolorizing carbon (30 g) and diatomaceous filter aid (24 g), and the solid removed by vacuum filtration and washed with water (420 mL).

(b) Conversion of Zwitterion to Dihydrochloride Monohydrate

The filtrate from part (a) above is cooled to 5° C. Aqueous hydrochloric acid (6N; 302.4 mL, 1.82 mole) followed by acetone (3.61 L) are then added while maintaining a temperature of 5°-9° C. After crystallization commences (various means for inducing crystallization may be desireable at this point such as seeding) the mixture is treated with aqueous hydrochloric acid (6N; 216 mL, 1.3 mole). The mixture is then stirred for 10 min, and treated with a further quantity of acetone (9.02 L) by addition during 1 h at 5°-8° C. The slurry is stirred for 1 h at 0°-5° C. and the product collected by filtration, washed with acetone (2×750 mL), and vacuum dried to constant weight at 45° C. (20 h). The dihydrochloride monohydrate is obtained as a white crystalline solid (259.7 g, 88.6% activity yield). The NMR and IR spectra confirmed the assigned structure; purity by HPLC analysis was 100%.

Anal. Calcd for $C_{19}H_{26}N_6O_5S_2Cl_2 \cdot H_2O$: C, 39.93; H, 4.94; N, 14.70; S, 11.22 Cl, 12.41; $H_2O$, 3.15; Found: C, 39.70; H, 4.80; N, 14.64; S, 11.12; Cl, 12.44; $H_2O$, 3.34.

X-Ray Diffraction Pattern

The X-ray diffraction pattern of the crystalline dihydrochloride monohydrate prepared as described in the preceeding Example XI was determined with a Rigaku Powder Diffractometer using a copper target X-ray tube, a nickel filter and the sample contained in a glass dish. The scan rate was 2°/min over the range from 5°-40° and a chart was mechanically recorded to show the angles of maximum diffraction. From this the (d) spacings and relative intensities ($I/I_o$) were calculated and are listed below:

X-RAY POWDER DIFFRACTION

Dihydrochloride Monohydrate

| d | $I/I_o$ (%) |
|---|---|
| 10.21 | 100 |
| 8.62 | 13 |
| 6.78 | 23 |
| 6.28 | 9 |
| 5.84 | 9 |
| 5.12 | 4 |
| 5.01 | 9 |
| 4.95 | 5 |
| 4.74 | 38 |
| 4.62 | 4 |
| 4.50 | 4 |
| 4.44 | 4 |
| 4.26 | 32 |
| 4.10 | 4 |
| 3.95 | 33 |
| 3.90 | 28 |
| 3.78 | 39 |
| 3.64 | 5 |
| 3.59 | 13 |
| 3.48 | 10 |
| 3.39 | 15 |
| 3.32 | 10 |
| 3.21 | 10 |
| 3.11 | 10 |
| 3.04 | 5 |
| 2.99 | 13 |
| 2.93 | 15 |
| 2.76 | 5 |
| 2.63 | 10 |
| 2.51 | 10 |
| 2.43 | 5 |
| 2.38 | 7 |

EXAMPLE XII

Preparation of Dihydrochloride Monohydrate from Sulfate - Resin Process

(a) Conversion of Sulfate to Zwitterion

The sulfate salt prepared as described in Example 1, (300 g, 0.518 mole), is added to a mechanically-stirred suspension of Dowex WGR resin (568.6 g, 1.762 mole) in Water for Injection, USP (690 mL) and the mixture stirred for 1 h at 20° C. The resin is a weak base epoxyamine polymer. After the mixing period, the resin is removed by vacuum filtration and washed with water (2×288 mL). The filtrate is treated with decolorizing carbon (15 g) and diatomaceous filter aid (7.5 g), and the solids then removed by filtration and washed with water (2×144 mL).

(b) Conversion of Zwitterion to Dihydrochloride Monohydrate

The filtrate from (a) above is converted in the same fashion as is described in Example XI (b) above. Other weak base water insoluble particulate ion exchange resins may be substituted for Dowex WGR in Example XII (a). In this example is Bio-Rad AG3-X4A which is a polystyrene divinylbenzene weak base resin.

The foregoing procedures of Examples XI and XII routinely produce monohydrate having a water content in the range of 2.46% to 3.70% with an average value of 3.31%. The value calculated from the stoichiometric formula is 3.15%. Drying at 57° C. in a desiccator at reduced pressure (0.001 mm Hg) over P₂O₅ for 5 days or at reduced pressure (10 mm Hg) at 45° C. for 2 days results in no loss in weight. Storage stability at 56° C. for 3 weeks produced a potency loss of 0.6%, and was substantially improved, therefore, as compared to the anhydrate (1.25% H₂O) described in Example V hereof (7.2% loss in 4 weeks at 56° C.).

The dihydrochloride monohydrate of Examples XI and XII was further characterized by thermogravemetric analysis (TGA) and by differential scanning calorimetry (DSC). The DSC curve is characterized by an onset peak temperature (exotherm) of 196.8° C. The TGA curve is characterized by a loss in weight (water of hydration) of 3.17% over the temperature range of 40.5° to 153.3° C. The theoretical weight loss is 3.15%. The latter behavior is typical of hydrates of known cephalosporin antibiotics.

The dihydrate of 7-[α-(2-aminothiazol-4-yl)-α-(Z)-methoxyiminoacetamido]-3-[(1-methyl-1-pyrrolidinio)-methyl]-3-cephem-4-carboxylate dihydrochloride is prepared by the hydration of the monohydrate described in Examples XI and XII by exposure to air having a relative humidity in excess of 70%. While the second molecule of water of hydration is not as tenaciously held in the dihydrate as is the case of the monohydrate, a consistent composition as determined by elemental analysis is uniformly obtained, and the dihydrate can be further distinguished from the monohydrate by DSC, TGA, and X-ray powder diffraction pattern.

EXAMPLE XIII

Preparation of Dihydrochloride Dihydrate

The dihydrochloride monohydrate prepared as described in Example XII is placed in a controlled humidity chamber at 80–93% relative humidity and 25°–37° C. for from 2 to 7 days. In each instance formation of the dihydrochloride dihydrate was established by analysis. Four samples prepared as described above revealed the following analytical results.

Analytical Results for Dihydrochloride Dihydrate

| Analyte | Theoretical Value | Sample Number | | | |
|---|---|---|---|---|---|
| | | 8-1B | 12-2 | 28-1 | 28-2 |
| Carbon | 38.71 | 38.76 | 38.64 | 38.74 | 38.53 |
| Hydrogen | 5.13 | 5.03 | 4.96 | 4.79 | 4.77 |
| Nitrogen | 14.26 | 14.22 | 14.19 | 14.24 | 14.18 |
| Sulfur | 10.88 | | | 10.66 | 10.22 |
| Chlorine | 12.03 | 11.90 | 11.84 | 12.12 | 11.90 |
| Water % | 6.11 | 6.16 | 6.99 | 6.34 | 6.11 |
| DSC endotherm °C. | | 81.6 | 84.6 | 85.6 | 84.6 |
| exotherm °C. | | 187.8 | 188.5 | 187.8 | 185.7 |
| TGA (% loss in weight) | | | | | |
| 25–68° C. | | 2.1 | 2.3 | 2.9 | 3.2 |
| 68–180° C. | | 3.4 | 3.5 | 3.1 | 3.1 |
| Total | | 5.5 | 5.8 | 6.0 | 6.3 |

*Karl Fisher method

The dihydrochloride dihydrate described in Example XIII can be easily dried to give the same dihydrochloride monohydrate described in Examples XI and XII. This can be accomplished by drying in vacuo or over a desiccant such as P₂O₅. The storage stability at elevated temperatures as measured by chemical and biological potency of the sample was similar for the monohydrate and dihydrate, but the formation of trace amounts of insoluble particles was observed with the dihydrate. Accordingly, the monohydrate carrying up to about 1% by weight of adventitious water is the preferred form (total water content ca. 2.5–4.1%). Such material when stored at 56° C. for 3 weeks exhibits at least a 96% retention of potency.

What is claimed is:

1. Temperature stable crystalline salts of 7-[α-(2-aminothiazol-4-yl)-α-(Z)-methoxyiminoacetamido]-3-[(1-methyl-1-pyrrolidinio)methyl]-3-cephem-4-carboxylate selected from the group consisting of the sulfuric, di-nitric, mono-hydrochloric, and di-hydrochloric acid addition salts, and orthophosphoric acid addition salts having 1.5–2 molar equivalents of H₃PO₄, or solvates thereof.

2. The crystalline salts of claim 1 selected from the group consisting of the sulfuric, mono-hydrochloric, di-hydrochloric and orthophosphoric acid addition salts, or solvates thereof.

3. The crystalline sulfuric acid addition salt of claim 1.

4. Crystalline 7-[α-(2-aminothiazol-4-yl)-α-(Z)-methoxyiminoacetamido-3-[1-methyl-1-pyrrolidinio)-methyl]-3-cephem-4-carboxylate sulfate salt having the following X-ray powder diffraction pattern.

| d spacing (Å) | I/I₀ (%) |
|---|---|
| 9.20 | 100 |
| 6.86 | 50 |
| 5.50 | 28 |
| 5.09 | 22 |
| 4.50 | 38 |
| 4.41 | 44 |
| 4.19 | 63 |
| 3.78 | 38 |
| 3.64 | 44 |
| 3.39 | 25 |
| 3.31 | 31 |
| 3.15 | 47 |

5. The crystalline orthophosphoric acid addition salt of claim 1, and hydrates thereof.

6. Crystalline 7-[α-(2-aminothiazol-4-yl)-α-(Z)-methoxyiminoacetamido]-3-[(1-methylpyrrolidinio)-methyl]-3-cephem-4-carboxylate phosphate having the following X-ray powder diffraction pattern.

| d | I/I₀ |
|---|---|
| 11.04 | 32 |
| 9.2 | 16 |
| 7.89 | 24 |
| 7.02 | 42 |
| 6.7 | 32 |
| 5.5 | 26 |
| 4.64 | 100 |
| 4.456 | 53 |
| 4.3 | 58 |
| 3.88 | 26 |
| 3.75 | 89 |
| 3.56 | 21 |
| 3.31 | 26 |
| 3.05 | 16 |

7. The crystalline 7-[α-(2-aminothiazol-4-yl)-α-(Z)-methoxyiminoacetamido]-3-[(1-methylpyrrolidinio)methyl]-3-cephem-4-carboxylate dihydrochloride of claim 1.

8. The crystalline 7-[α-(2-aminothiazol-4-yl)-α-(Z)-methoxyiminoacetamido]-3-[(1-methylpyrrolidinio)- methyl-3-cephem-4-carboxylate dihydrochloride hydrate of claim 1 containing from 2.5% to 7.0% by weight of water.

9. The crystalline 7-[α-(2-aminothiazol-4-yl)-α-(Z)-methoxyiminoacetamido]-3-[(1-methylpyrrolidinio)methyl]-3-cephem-4-carboxylate dihydrochloride monohydrate of claim 1 containing from 2.5 to 4.1% by weight of water.

10. The crystalline 7-[α-(2-aminothiazol-4-yl)-α-(Z)-methoxyiminoacetamido]-3-[(1-methylpyrrolidinio)methyl]-3-cephem-4-carboxylate dihydrochloride monohydrate of claim 1 having the following X-ray powder diffraction pattern

X-RAY POWDER DIFFRACTION

Dihydrochloride Monohydrate

| d | $I/I_o$ (%) |
|---|---|
| 10.21 | 100 |
| 8.62 | 13 |
| 6.78 | 23 |
| 6.28 | 9 |
| 5.84 | 9 |
| 5.12 | 4 |
| 5.01 | 9 |
| 4.95 | 5 |
| 4.74 | 38 |
| 4.62 | 4 |
| 4.50 | 4 |
| 4.44 | 4 |
| 4.26 | 32 |
| 4.10 | 4 |
| 3.95 | 33 |
| 3.90 | 28 |
| 3.78 | 39 |
| 3.64 | 5 |
| 3.59 | 13 |
| 3.48 | 10 |
| 3.39 | 15 |
| 3.32 | 10 |
| 3.21 | 10 |
| 3.11 | 10 |
| 3.04 | 5 |
| 2.99 | 13 |
| 2.93 | 15 |
| 2.76 | 5 |
| 2.63 | 10 |
| 2.51 | 10 |
| 2.43 | 5 |
| 2.38 | 7 |

* * * * *

UNITED STATES PATENT AND TRADEMARK OFFICE
CERTIFICATE OF CORRECTION

PATENT NO. : 4,910,301
DATED     : March 20, 1990
INVENTOR(S) : Murray A. Kaplan, Thomas W. Hudyma; ROBERT A. LIPPER; KUN M. SHIH; and SUSAN D. BOETTGER It is certified that error appears in the above-indentified patent and that said Letters Patent is hereby corrected as shown below:

col. 6, lines 57-61, delete "Analysis: Calculated for $C_{19}H_{24}N_6O_5S_2 \cdot HCl$: %C, 41.37; %H, 4.75; %N, 15.2; %S, 11.63; %Cl, 12.86. Found: %C, 39.32; %H, 4.88; %N, 13.95; %S, 11.28; %Cl, 12.44; %$H_2O$, 4.5. (Corrected for $H_2O$: %C, 41.17; %N, 14.61; %S, 11.82; %Cl, 13.03)."

Signed and Sealed this

Twenty-sixth Day of October, 1993

Attest:

BRUCE LEHMAN

Attesting Officer

Commissioner of Patents and Trademarks